United States Patent
Louis et al.

(10) Patent No.: US 9,078,765 B2
(45) Date of Patent: *Jul. 14, 2015

(54) VERTEBRAL CAGE DEVICE WITH MODULAR FIXATION

(75) Inventors: Christian Louis, Aubagne (FR); Jean Huppert, L'Etrat (FR); Patrick Tropiano, Marseilles (FR); Thierry Dufour, Olivet (FR)

(73) Assignee: LDR Medical, Rosieres Pres Troyes (FR)

( * ) Notice: Subject to any disclaimer, the term of this patent is extended or adjusted under 35 U.S.C. 154(b) by 465 days.

This patent is subject to a terminal disclaimer.

(21) Appl. No.: 13/438,352

(22) Filed: Apr. 3, 2012

(65) Prior Publication Data

US 2012/0191196 A1    Jul. 26, 2012

Related U.S. Application Data

(63) Continuation of application No. 12/430,768, filed on Apr. 27, 2009, now Pat. No. 8,147,556, which is a continuation of application No. 10/483,563, filed as application No. PCT/IB02/03390 on Jul. 12, 2002, now Pat. No. 7,594,931.

(30) Foreign Application Priority Data

Jul. 13, 2001    (FR) .................................... 01 09381

(51) Int. Cl.
*A61F 2/44* (2006.01)
*A61B 17/064* (2006.01)
(Continued)

(52) U.S. Cl.
CPC ........... *A61F 2/4455* (2013.01); *A61B 17/0642* (2013.01); *A61B 17/7059* (2013.01);
(Continued)

(58) Field of Classification Search
CPC ........... A61F 2/4455; A61F 2250/0098; A61F 2/4465; A61F 2002/2835; A61F 2002/3008; A61F 2002/30131; A61F 2002/30472; A61F 2002/305; A61F 2002/30578; A61F 2002/30604; A61F 2002/448; A61F 2220/0025; A61F 2220/0041; A61F 2230/0013; A61B 17/0642; A61B 2017/0648; A61B 17/86; A61B 17/7059
USPC ............. 623/17.11–17.16; 606/246, 247, 280
See application file for complete search history.

(56) References Cited

U.S. PATENT DOCUMENTS

| | | |
|---|---|---|
| 3,374,786 A | 3/1968 | Callender, Jr. |
| 3,791,380 A | 2/1974 | Dawidowski |

(Continued)

FOREIGN PATENT DOCUMENTS

| | | |
|---|---|---|
| DE | 3741493 | 6/1989 |
| DE | 20320454 | 10/2004 |

(Continued)

OTHER PUBLICATIONS

European Patent Office; Office Action for App. No. 02784881, Pub'n. No. EP1406563; Mar. 13, 2009; EPO; Munich, Germany; all pages.

(Continued)

*Primary Examiner* — Pedro Philogene
(74) *Attorney, Agent, or Firm* — Denko Coburn Lauff LLP

(57) ABSTRACT

Intervertebral arthrodesis for insertion in an intervertebral space separating opposite faces of two adjacent vertebrae has a ring shaped intervertebral cage having a bar that extends perpendicular to the axis of the spine. The bar has a height less than the rest of the cage. A surface of the cage contacting the vertebrae has an undulating shape for limiting sliding of the cage in a plane parallel to the vertebrae faces.

20 Claims, 5 Drawing Sheets

(51) Int. Cl.
  *A61B 17/70* (2006.01)
  *A61B 17/86* (2006.01)
  *A61F 2/28* (2006.01)
  *A61F 2/30* (2006.01)

(52) U.S. Cl.
  CPC ........ *A61B 17/86* (2013.01); *A61B 2017/0648* (2013.01); *A61F 2/4465* (2013.01); *A61F 2002/2835* (2013.01); *A61F 2002/305* (2013.01); *A61F 2002/3008* (2013.01); *A61F 2002/30131* (2013.01); *A61F 2002/30472* (2013.01); *A61F 2002/30578* (2013.01); *A61F 2002/30604* (2013.01); *A61F 2002/448* (2013.01); *A61F 2220/0025* (2013.01); *A61F 2220/0041* (2013.01); *A61F 2230/0013* (2013.01); *A61F 2250/0098* (2013.10)

(56) References Cited

U.S. PATENT DOCUMENTS

| | | |
|---|---|---|
| 3,892,232 A | 7/1975 | Neufeld |
| 4,009,712 A | 3/1977 | Burstein et al. |
| 4,135,506 A | 1/1979 | Ulrich |
| 4,175,555 A | 11/1979 | Herbert |
| 4,237,875 A | 12/1980 | Termanini |
| 4,379,451 A | 4/1983 | Getscher |
| 4,409,974 A | 10/1983 | Freedland |
| 4,432,358 A | 2/1984 | Fixel |
| 4,488,543 A | 12/1984 | Tornier |
| 4,494,535 A | 1/1985 | Haig |
| 4,519,100 A | 5/1985 | Wills et al. |
| 4,561,432 A | 12/1985 | Mazor |
| 4,599,086 A | 7/1986 | Doty |
| 4,612,920 A | 9/1986 | Lower |
| 4,621,629 A | 11/1986 | Koeneman |
| 4,632,101 A | 12/1986 | Freedland |
| 4,653,489 A | 3/1987 | Tronzo |
| 4,657,001 A | 4/1987 | Fixel |
| 4,721,103 A | 1/1988 | Freedland |
| 4,759,352 A | 7/1988 | Lozier |
| 4,787,378 A | 11/1988 | Sodhi |
| 4,790,303 A | 12/1988 | Steffee |
| 4,791,918 A | 12/1988 | Von Hasselbach |
| 4,892,545 A | 1/1990 | Day et al. |
| 4,898,156 A | 2/1990 | Gatturna et al. |
| 4,904,261 A | 2/1990 | Dove et al. |
| 4,946,468 A | 8/1990 | Li |
| 4,964,403 A | 10/1990 | Karas et al. |
| 4,968,315 A | 11/1990 | Gatturna |
| 4,969,887 A | 11/1990 | Sodhi |
| 4,973,332 A | 11/1990 | Kummer |
| 4,973,333 A | 11/1990 | Treharne |
| 5,002,550 A | 3/1991 | Li |
| 5,007,910 A | 4/1991 | Anapliotis et al. |
| 5,032,125 A | 7/1991 | Durham et al. |
| 5,041,114 A | 8/1991 | Chapman et al. |
| 5,041,116 A | 8/1991 | Wilson |
| 5,046,513 A | 9/1991 | Gatturna et al. |
| 5,057,103 A | 10/1991 | Davis |
| 5,062,851 A | 11/1991 | Branemark |
| 5,087,266 A | 2/1992 | Connell et al. |
| 5,098,433 A | 3/1992 | Freedland |
| 5,116,336 A | 5/1992 | Frigg |
| 5,129,901 A | 7/1992 | Decoste |
| 5,176,681 A | 1/1993 | Lawes et al. |
| 5,192,303 A | 3/1993 | Gatturna et al. |
| 5,207,679 A | 5/1993 | Li |
| 5,217,486 A | 6/1993 | Rice et al. |
| 5,242,448 A | 9/1993 | Pettine et al. |
| 5,300,074 A | 4/1994 | Frigg |
| 5,324,292 A | 6/1994 | Meyers |
| 5,342,394 A | 8/1994 | Matsuno et al. |
| 5,356,410 A | 10/1994 | Pennig |
| 5,356,413 A | 10/1994 | Martins et al. |
| 5,372,599 A | 12/1994 | Martins |
| 5,397,364 A * | 3/1995 | Kozak et al. ............... 623/17.11 |
| 5,417,692 A | 5/1995 | Goble et al. |
| 5,417,712 A | 5/1995 | Whittaker et al. |
| 5,429,641 A | 7/1995 | Gotfried |
| 5,437,674 A | 8/1995 | Worcel et al. |
| 5,443,514 A | 8/1995 | Steffee |
| 5,456,721 A | 10/1995 | Legrand |
| 5,458,601 A | 10/1995 | Young, Jr. et al. |
| 5,472,452 A | 12/1995 | Trott |
| 5,478,342 A | 12/1995 | Kohrs |
| 5,489,210 A | 2/1996 | Hanosh |
| 5,507,754 A | 4/1996 | Green et al. |
| 5,522,845 A | 6/1996 | Wenstrom, Jr. |
| 5,522,899 A | 6/1996 | Michelson |
| 5,531,792 A | 7/1996 | Huene |
| 5,534,004 A | 7/1996 | Santangelo |
| 5,549,617 A | 8/1996 | Green et al. |
| 5,562,689 A | 10/1996 | Green et al. |
| 5,571,104 A | 11/1996 | Li |
| 5,571,109 A | 11/1996 | Bertagnoli |
| 5,571,189 A | 11/1996 | Kuslich |
| 5,578,035 A | 11/1996 | Lin |
| 5,591,168 A | 1/1997 | Judet et al. |
| 5,593,409 A | 1/1997 | Michelson |
| 5,609,635 A | 3/1997 | Michelson |
| 5,613,974 A | 3/1997 | Andreas et al. |
| 5,620,012 A | 4/1997 | Benderev et al. |
| 5,643,321 A | 7/1997 | McDevitt |
| 5,702,449 A | 12/1997 | McKay |
| 5,766,253 A | 6/1998 | Brosnahan, III |
| 5,782,830 A | 7/1998 | Farris |
| 5,800,547 A | 9/1998 | Schafer et al. |
| 5,888,222 A | 3/1999 | Coates et al. |
| 5,888,227 A | 3/1999 | Cottle |
| 5,895,427 A | 4/1999 | Kuslich et al. |
| 5,968,098 A | 10/1999 | Winslow |
| 5,980,522 A | 11/1999 | Koros et al. |
| 5,989,289 A | 11/1999 | Coates et al. |
| 6,066,174 A | 5/2000 | Farris |
| 6,066,175 A | 5/2000 | Henderson et al. |
| 6,099,531 A | 8/2000 | Bonutti |
| 6,102,950 A | 8/2000 | Vaccaro |
| 6,129,763 A | 10/2000 | Chauvin et al. |
| 6,143,032 A | 11/2000 | Schafer et al. |
| 6,174,311 B1 | 1/2001 | Branch et al. |
| 6,179,873 B1 | 1/2001 | Zientek |
| 6,206,923 B1 | 3/2001 | Boyd et al. |
| 6,214,050 B1 | 4/2001 | Huene |
| 6,241,733 B1 | 6/2001 | Nicholson et al. |
| 6,258,094 B1 | 7/2001 | Nicholson et al. |
| 6,261,293 B1 | 7/2001 | Nicholson et al. |
| 6,261,295 B1 | 7/2001 | Nicholson et al. |
| 6,267,764 B1 | 7/2001 | Elberg |
| 6,371,987 B1 | 4/2002 | Weiland et al. |
| 6,419,703 B1 | 7/2002 | Fallin et al. |
| 6,423,063 B1 | 7/2002 | Bonutti |
| 6,447,546 B1 * | 9/2002 | Bramlet et al. ............. 623/17.16 |
| 6,482,584 B1 | 11/2002 | Mills et al. |
| 6,485,517 B1 | 11/2002 | Michelson |
| 6,497,726 B1 | 12/2002 | Carter et al. |
| 6,540,753 B2 | 4/2003 | Cohen |
| 6,558,423 B1 | 5/2003 | Michelson |
| 6,565,605 B2 | 5/2003 | Goble et al. |
| 6,607,530 B1 | 8/2003 | Carl et al. |
| 6,610,065 B1 | 8/2003 | Branch et al. |
| 6,613,278 B1 | 9/2003 | Mills et al. |
| 6,635,086 B2 | 10/2003 | Lin |
| 6,648,893 B2 | 11/2003 | Dudasik |
| 6,652,818 B1 | 11/2003 | Mills et al. |
| 6,706,067 B2 | 3/2004 | Shimp et al. |
| 6,723,128 B2 | 4/2004 | Uk |
| 6,770,096 B2 | 8/2004 | Bolger et al. |
| 6,805,713 B1 | 10/2004 | Carter et al. |
| 6,805,714 B2 | 10/2004 | Sutcliffe |
| 6,808,537 B2 | 10/2004 | Michelson |
| 6,835,206 B2 | 12/2004 | Jackson |
| 6,849,093 B2 | 2/2005 | Michelson |
| 6,890,355 B2 | 5/2005 | Michelson |

(56) References Cited

U.S. PATENT DOCUMENTS

| | | | |
|---|---|---|---|
| 6,902,580 B2 | 6/2005 | Fallin et al. | |
| 6,923,811 B1 | 8/2005 | Carl et al. | |
| 6,923,830 B2 | 8/2005 | Michelson | |
| 6,955,691 B2 | 10/2005 | Chae et al. | |
| 6,962,606 B2 | 11/2005 | Michelson | |
| 6,964,687 B1 * | 11/2005 | Bernard et al. | 623/17.16 |
| 6,972,019 B2 | 12/2005 | Michelson | |
| 6,972,035 B2 | 12/2005 | Michelson | |
| 6,981,975 B2 | 1/2006 | Michelson | |
| 6,984,234 B2 | 1/2006 | Bray | |
| 6,994,727 B2 | 2/2006 | Khandkar et al. | |
| 7,001,385 B2 | 2/2006 | Bonutti | |
| 7,008,453 B1 | 3/2006 | Michelson | |
| 7,018,412 B2 | 3/2006 | Ferreira et al. | |
| 7,033,394 B2 | 4/2006 | Michelson | |
| 7,041,135 B2 | 5/2006 | Michelson | |
| 7,041,136 B2 | 5/2006 | Goble et al. | |
| 7,048,762 B1 | 5/2006 | Sander et al. | |
| 7,048,765 B1 | 5/2006 | Grooms et al. | |
| 7,060,097 B2 | 6/2006 | Fraser et al. | |
| 7,063,701 B2 | 6/2006 | Michelson | |
| 7,063,702 B2 | 6/2006 | Michelson | |
| 7,066,961 B2 | 6/2006 | Michelson | |
| 7,074,237 B2 | 7/2006 | Goble et al. | |
| 7,090,698 B2 | 8/2006 | Goble et al. | |
| 7,094,239 B1 | 8/2006 | Michelson | |
| 7,112,206 B2 | 9/2006 | Michelson | |
| 7,118,579 B2 | 10/2006 | Michelson | |
| 7,118,598 B2 | 10/2006 | Michelson | |
| 7,128,760 B2 | 10/2006 | Michelson | |
| 7,128,761 B2 | 10/2006 | Kuras et al. | |
| 7,153,325 B2 | 12/2006 | Kim et al. | |
| 7,163,561 B2 | 1/2007 | Michelson | |
| 7,211,112 B2 | 5/2007 | Baynham et al. | |
| 7,217,291 B2 | 5/2007 | Zucherman et al. | |
| 7,217,293 B2 | 5/2007 | Branch, Jr. | |
| 7,223,289 B2 | 5/2007 | Trieu et al. | |
| 7,232,464 B2 | 6/2007 | Mathieu et al. | |
| 7,235,082 B2 | 6/2007 | Bartish et al. | |
| 7,276,081 B1 | 10/2007 | Coates et al. | |
| 7,291,170 B2 | 11/2007 | Huppert | |
| 7,326,248 B2 | 2/2008 | Michelson | |
| 7,361,196 B2 | 4/2008 | Fallin et al. | |
| 7,410,501 B2 | 8/2008 | Michelson | |
| 7,431,735 B2 | 10/2008 | Liu et al. | |
| 7,435,262 B2 | 10/2008 | Michelson | |
| 7,442,209 B2 | 10/2008 | Michelson | |
| 7,445,635 B2 | 11/2008 | Fallin et al. | |
| 7,445,636 B2 | 11/2008 | Michelson | |
| 7,455,692 B2 | 11/2008 | Michelson | |
| 7,465,317 B2 | 12/2008 | Malberg et al. | |
| 7,479,160 B2 | 1/2009 | Branch et al. | |
| 7,503,933 B2 | 3/2009 | Michelson | |
| 7,540,882 B2 | 6/2009 | Michelson | |
| 7,566,345 B1 | 7/2009 | Fallin et al. | |
| 7,588,590 B2 | 9/2009 | Chervitz et al. | |
| 7,591,851 B2 | 9/2009 | Winslow et al. | |
| 7,594,931 B2 * | 9/2009 | Louis et al. | 623/17.11 |
| 7,594,932 B2 | 9/2009 | Aferzon et al. | |
| 7,601,170 B2 | 10/2009 | Winslow et al. | |
| 7,604,654 B2 | 10/2009 | Fallin et al. | |
| 7,608,107 B2 | 10/2009 | Michelson | |
| 7,618,453 B2 | 11/2009 | Goble et al. | |
| 7,618,455 B2 | 11/2009 | Goble et al. | |
| 7,618,456 B2 | 11/2009 | Mathieu et al. | |
| 7,621,955 B2 | 11/2009 | Goble et al. | |
| 7,621,958 B2 | 11/2009 | Zdeblick et al. | |
| 7,625,393 B2 | 12/2009 | Fallin et al. | |
| 7,637,951 B2 | 12/2009 | Michelson | |
| 7,637,953 B2 | 12/2009 | Branch et al. | |
| 7,637,954 B2 | 12/2009 | Michelson | |
| 7,641,690 B2 | 1/2010 | Abdou | |
| 7,655,027 B2 | 2/2010 | Michelson | |
| 7,658,766 B2 | 2/2010 | Melkent et al. | |
| 7,682,396 B2 | 3/2010 | Beaurain et al. | |
| 7,695,516 B2 | 4/2010 | Zeegers | |
| 7,695,517 B2 | 4/2010 | Benzel et al. | |
| 7,727,280 B2 | 6/2010 | McLuen | |
| 7,744,602 B2 | 6/2010 | Teeny et al. | |
| 7,749,252 B2 | 7/2010 | Zucherman et al. | |
| 7,749,274 B2 | 7/2010 | Razian | |
| 7,753,937 B2 | 7/2010 | Chervitz et al. | |
| 7,771,473 B2 | 8/2010 | Thramann | |
| 7,771,475 B2 | 8/2010 | Michelson | |
| 7,776,090 B2 | 8/2010 | Winslow et al. | |
| 7,780,670 B2 | 8/2010 | Bonutti | |
| 7,789,914 B2 | 9/2010 | Michelson | |
| 7,794,502 B2 | 9/2010 | Michelson | |
| 7,799,053 B2 | 9/2010 | Haid, Jr. et al. | |
| 7,799,057 B2 | 9/2010 | Hudgins et al. | |
| 7,799,081 B2 | 9/2010 | McKinley | |
| 7,811,326 B2 | 10/2010 | Braddock, Jr. et al. | |
| 7,819,903 B2 | 10/2010 | Fraser et al. | |
| 7,824,445 B2 | 11/2010 | Biro et al. | |
| 7,833,255 B2 | 11/2010 | Chow et al. | |
| 7,842,088 B2 | 11/2010 | Rashbaum et al. | |
| 7,846,207 B2 | 12/2010 | Lechmann et al. | |
| 7,850,731 B2 | 12/2010 | Brittan et al. | |
| 7,850,732 B2 | 12/2010 | Heinz | |
| 7,850,733 B2 | 12/2010 | Baynham et al. | |
| 7,862,616 B2 | 1/2011 | Lechmann et al. | |
| 7,871,441 B2 | 1/2011 | Eckman | |
| 7,875,076 B2 | 1/2011 | Mathieu et al. | |
| 7,887,591 B2 | 2/2011 | Aebi et al. | |
| 7,892,261 B2 | 2/2011 | Bonutti | |
| 7,892,286 B2 | 2/2011 | Michelson | |
| 7,909,871 B2 | 3/2011 | Abdou | |
| 7,914,560 B2 | 3/2011 | Hoy et al. | |
| 7,922,729 B2 | 4/2011 | Michelson | |
| 7,931,674 B2 | 4/2011 | Zucherman et al. | |
| 7,931,840 B2 | 4/2011 | Michelson | |
| 7,935,149 B2 | 5/2011 | Michelson | |
| 7,951,198 B2 | 5/2011 | Sucec et al. | |
| 7,955,390 B2 | 6/2011 | Fallin et al. | |
| 7,972,337 B2 | 7/2011 | Boyajian et al. | |
| 7,972,363 B2 | 7/2011 | Moskowitz et al. | |
| 7,972,365 B2 | 7/2011 | Michelson | |
| 7,976,566 B2 | 7/2011 | Michelson | |
| 7,985,255 B2 | 7/2011 | Bray et al. | |
| 7,985,258 B2 | 7/2011 | Zdeblick et al. | |
| 7,993,373 B2 | 8/2011 | Hoy et al. | |
| 7,998,177 B2 | 8/2011 | Hoy et al. | |
| 7,998,178 B2 | 8/2011 | Hoy et al. | |
| 8,007,534 B2 | 8/2011 | Michelson | |
| 8,021,401 B2 | 9/2011 | Carl et al. | |
| 8,021,430 B2 | 9/2011 | Michelson | |
| 8,043,334 B2 | 10/2011 | Fisher et al. | |
| 8,062,336 B2 | 11/2011 | Triplett et al. | |
| 8,062,375 B2 | 11/2011 | Glerum et al. | |
| 8,066,741 B2 | 11/2011 | Fallin et al. | |
| 8,066,749 B2 | 11/2011 | Winslow et al. | |
| 8,070,816 B2 | 12/2011 | Taylor | |
| 8,070,819 B2 | 12/2011 | Aferzon et al. | |
| 8,075,593 B2 | 12/2011 | Hess | |
| 8,075,618 B2 | 12/2011 | Trieu et al. | |
| 8,075,621 B2 | 12/2011 | Michelson | |
| 8,097,034 B2 | 1/2012 | Michelson | |
| 8,114,082 B2 | 2/2012 | Boyajian et al. | |
| 8,118,873 B2 | 2/2012 | Humphreys et al. | |
| 8,137,405 B2 | 3/2012 | Kostuik et al. | |
| 8,147,556 B2 * | 4/2012 | Louis et al. | 623/17.16 |
| 8,167,946 B2 | 5/2012 | Michelson | |
| 8,167,949 B2 | 5/2012 | Tyber et al. | |
| 8,167,950 B2 | 5/2012 | Aferzon et al. | |
| 8,182,539 B2 | 5/2012 | Tyber et al. | |
| 8,187,329 B2 | 5/2012 | Theofilos | |
| 8,187,332 B2 | 5/2012 | McLuen | |
| 8,216,312 B2 | 7/2012 | Gray | |
| 8,241,359 B2 | 8/2012 | Davis et al. | |
| 8,267,999 B2 * | 9/2012 | Beaurain et al. | 623/17.14 |
| 8,313,528 B1 | 11/2012 | Wensel | |
| 8,343,219 B2 | 1/2013 | Allain et al. | |
| 8,696,681 B2 | 4/2014 | Harris et al. | |
| 2001/0018614 A1 | 8/2001 | Bianchi | |

(56) References Cited

U.S. PATENT DOCUMENTS

| | | |
|---|---|---|
| 2001/0031254 A1 | 10/2001 | Bianchi et al. |
| 2001/0031967 A1 | 10/2001 | Nicholson et al. |
| 2002/0016592 A1 | 2/2002 | Branch et al. |
| 2002/0026243 A1 | 2/2002 | Lin |
| 2002/0032483 A1 | 3/2002 | Nicholson et al. |
| 2002/0040243 A1 | 4/2002 | Attali et al. |
| 2002/0070565 A1 | 6/2002 | Szapucki et al. |
| 2002/0072806 A1 | 6/2002 | Buskirk et al. |
| 2002/0082700 A1 | 6/2002 | Bianchi et al. |
| 2002/0106393 A1 | 8/2002 | Bianchi et al. |
| 2002/0119437 A1 | 8/2002 | Grooms et al. |
| 2002/0138143 A1 | 9/2002 | Grooms et al. |
| 2002/0161444 A1 | 10/2002 | Choi |
| 2002/0165612 A1 | 11/2002 | Gerber et al. |
| 2002/0165613 A1 | 11/2002 | Lin et al. |
| 2003/0023304 A1 | 1/2003 | Carter et al. |
| 2003/0027125 A1 | 2/2003 | Mills et al. |
| 2003/0060886 A1 | 3/2003 | Van Hoeck et al. |
| 2003/0069640 A1 | 4/2003 | Ferreira et al. |
| 2003/0074075 A1 | 4/2003 | Thomas, Jr. et al. |
| 2003/0097179 A1 | 5/2003 | Carter et al. |
| 2003/0100950 A1 | 5/2003 | Moret |
| 2003/0135279 A1 | 7/2003 | Michelson |
| 2003/0139815 A1 | 7/2003 | Grooms et al. |
| 2003/0149438 A1 | 8/2003 | Nichols et al. |
| 2003/0187436 A1 | 10/2003 | Bolger et al. |
| 2003/0195514 A1 | 10/2003 | Trieu et al. |
| 2003/0195629 A1 | 10/2003 | Pafford et al. |
| 2003/0233147 A1 | 12/2003 | Nicholson et al. |
| 2004/0010312 A1 | 1/2004 | Enayati |
| 2004/0030387 A1 | 2/2004 | Landry et al. |
| 2004/0073307 A1 | 4/2004 | Keller |
| 2004/0073313 A1 | 4/2004 | Link et al. |
| 2004/0093083 A1 | 5/2004 | Branch et al. |
| 2004/0097929 A1 | 5/2004 | Branch et al. |
| 2004/0115172 A1 | 6/2004 | Bianchi et al. |
| 2004/0117022 A1 | 6/2004 | Marnay et al. |
| 2004/0127990 A1 | 7/2004 | Bartish, Jr. et al. |
| 2004/0210219 A1 | 10/2004 | Bray |
| 2004/0210308 A1 | 10/2004 | Carter et al. |
| 2004/0210313 A1 | 10/2004 | Michelson |
| 2004/0230306 A1 | 11/2004 | Hoeck et al. |
| 2004/0243238 A1 | 12/2004 | Arnin et al. |
| 2004/0243240 A1 | 12/2004 | Beaurain et al. |
| 2004/0254643 A1 | 12/2004 | Jackson |
| 2005/0004672 A1 | 1/2005 | Pafford et al. |
| 2005/0015149 A1 | 1/2005 | Michelson |
| 2005/0027359 A1 | 2/2005 | Mashburn |
| 2005/0027360 A1 | 2/2005 | Webb et al. |
| 2005/0038512 A1 | 2/2005 | Michelson |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0085917 A1 | 4/2005 | Marnay et al. |
| 2005/0096742 A1 | 5/2005 | Mills et al. |
| 2005/0096745 A1 | 5/2005 | Andre et al. |
| 2005/0100862 A1 | 5/2005 | Mills et al. |
| 2005/0101957 A1 | 5/2005 | Buskirk et al. |
| 2005/0119744 A1 | 6/2005 | Buskirk et al. |
| 2005/0119747 A1 | 6/2005 | Fabris Monterumici et al. |
| 2005/0143733 A1 | 6/2005 | Petit |
| 2005/0143825 A1 | 6/2005 | Enayati |
| 2005/0149189 A1 | 7/2005 | Mokhtar et al. |
| 2005/0165483 A1 | 7/2005 | Ray, III et al. |
| 2005/0171554 A1 | 8/2005 | Estes et al. |
| 2005/0288788 A1 | 12/2005 | Dougherty-Shah |
| 2006/0058878 A1 | 3/2006 | Michelson |
| 2006/0069437 A1 | 3/2006 | Weber |
| 2006/0085076 A1 | 4/2006 | Krishna et al. |
| 2006/0089717 A1 | 4/2006 | Krishna et al. |
| 2006/0095136 A1 | 5/2006 | McLuen |
| 2006/0122703 A1 | 6/2006 | Aebi et al. |
| 2006/0129244 A1 | 6/2006 | Ensign |
| 2006/0136063 A1 | 6/2006 | Zeegers |
| 2006/0155377 A1 | 7/2006 | Beaurain et al. |
| 2006/0206208 A1 | 9/2006 | Michelson |
| 2006/0235426 A1 | 10/2006 | Lim et al. |
| 2006/0241761 A1 | 10/2006 | Gately |
| 2006/0241764 A1 | 10/2006 | Michelson |
| 2006/0253201 A1 | 11/2006 | McLuen |
| 2007/0016297 A1 | 1/2007 | Johnson |
| 2007/0032871 A1 | 2/2007 | Michelson |
| 2007/0073404 A1 | 3/2007 | Rashbaum et al. |
| 2007/0093850 A1 | 4/2007 | Harris et al. |
| 2007/0142843 A1 | 6/2007 | Dye |
| 2007/0162128 A1 | 7/2007 | DeRidder et al. |
| 2007/0179623 A1 | 8/2007 | Trieu et al. |
| 2007/0250167 A1 | 10/2007 | Bray et al. |
| 2007/0260249 A1 | 11/2007 | Boyajian et al. |
| 2007/0270951 A1 | 11/2007 | Davis et al. |
| 2007/0270954 A1 | 11/2007 | Wu |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2008/0021562 A1 | 1/2008 | Huppert |
| 2008/0027547 A1 | 1/2008 | Yu et al. |
| 2008/0027550 A1 | 1/2008 | Link et al. |
| 2008/0033562 A1 | 2/2008 | Krishna et al. |
| 2008/0051887 A1 | 2/2008 | Carter et al. |
| 2008/0109083 A1 | 5/2008 | Van Hoeck et al. |
| 2008/0125865 A1 | 5/2008 | Abdelgany |
| 2008/0161933 A1 | 7/2008 | Grotz et al. |
| 2008/0195211 A1 | 8/2008 | Lin et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0186333 A1 | 7/2009 | Mills et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0222092 A1 | 9/2009 | Davis et al. |
| 2009/0222100 A1 | 9/2009 | Cipoletti et al. |
| 2009/0234455 A1 | 9/2009 | Moskowitz et al. |
| 2009/0265007 A1 | 10/2009 | Colleran |
| 2009/0270990 A1 | 10/2009 | Louis et al. |
| 2010/0004664 A1 | 1/2010 | Boyajian et al. |
| 2010/0049259 A1 | 2/2010 | Lambrecht et al. |
| 2010/0057206 A1 | 3/2010 | Duffield et al. |
| 2010/0057207 A1 | 3/2010 | Ray, III et al. |
| 2010/0063554 A1 | 3/2010 | Branch et al. |
| 2010/0070037 A1 | 3/2010 | Parry et al. |
| 2010/0082104 A1 | 4/2010 | Carter et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |

(56) References Cited

U.S. PATENT DOCUMENTS

| | | | |
|---|---|---|---|
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0217396 A1 | 8/2010 | Bianchi et al. |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0268349 A1 | 10/2010 | Bianchi et al. |
| 2010/0286777 A1 | 11/2010 | Errico et al. |
| 2010/0286787 A1 | 11/2010 | Villiers et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0196492 A1 | 8/2011 | Lambrecht et al. |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0230971 A1 | 9/2011 | Donner et al. |
| 2011/0264227 A1 | 10/2011 | Boyajian et al. |
| 2011/0295371 A1 | 12/2011 | Moskowitz et al. |
| 2011/0301707 A1 | 12/2011 | Buskirk et al. |
| 2011/0301713 A1 | 12/2011 | Theofilos |
| 2011/0301714 A1 | 12/2011 | Theofilos |
| 2011/0313528 A1 | 12/2011 | Laubert et al. |
| 2012/0004660 A1 | 1/2012 | Grooms et al. |
| 2012/0116466 A1 | 5/2012 | Dinville et al. |
| 2012/0191196 A1 | 7/2012 | Louis et al. |

FOREIGN PATENT DOCUMENTS

| | | |
|---|---|---|
| DE | 10323363 | 12/2004 |
| EP | 0637439 | 2/1995 |
| EP | 0697200 | 2/1996 |
| EP | 0951879 | 10/1999 |
| EP | 0965313 | 12/1999 |
| EP | 2113228 | 11/2009 |
| EP | 2327375 | 6/2011 |
| EP | 2340788 | 7/2011 |
| EP | 2363080 | 9/2011 |
| FR | 2703580 | 10/1994 |
| FR | 2733413 | 10/1996 |
| FR | 2808995 | 11/2001 |
| FR | 2823095 | 10/2002 |
| FR | 2827156 | 1/2003 |
| FR | 2846550 | 5/2004 |
| FR | 2861582 | 5/2005 |
| FR | 2879436 | 6/2006 |
| FR | 2880795 | 7/2006 |
| FR | 2891135 | 3/2007 |
| FR | 2897259 | 8/2007 |
| FR | 2916956 | 12/2008 |
| FR | 2987256 | 8/2013 |
| WO | WO9508306 | 3/1995 |
| WO | WO9715248 | 5/1997 |
| WO | WO9801091 | 1/1998 |
| WO | WO9855052 | 12/1998 |
| WO | WO9909914 | 3/1999 |
| WO | WO9963914 | 12/1999 |
| WO | WO0024327 | 5/2000 |
| WO | WO0170141 | 9/2001 |
| WO | WO0187194 | 11/2001 |
| WO | WO0213732 | 2/2002 |
| WO | WO02058599 | 8/2002 |
| WO | WO02089701 | 11/2002 |
| WO | WO03005939 | 1/2003 |
| WO | WO2004034935 | 4/2004 |
| WO | WO2004041129 | 5/2004 |
| WO | WO2004089256 | 10/2004 |
| WO | WO2006047587 | 5/2006 |
| WO | WO2006120505 | 11/2006 |
| WO | WO2007078978 | 7/2007 |
| WO | WO2007093900 | 8/2007 |
| WO | WO2008149223 | 12/2008 |
| WO | WO2009033100 | 3/2009 |
| WO | WO2010090801 | 8/2010 |
| WO | WO2011080535 | 7/2011 |
| WO | WO2011129973 | 10/2011 |
| WO | WO2013124453 | 8/2013 |

OTHER PUBLICATIONS

LDR Medical, by its attorneys; Reply to Office Action for App. No. 02784881, Pub'n. No. EP1406563; Jul. 22, 2009; EPO; Munich, Germany; all pages.

European Patent Office; Office Action for App. No. 02784881, Pub'n. No. EP1406563; Aug. 4, 2009; EPO; Munich, Germany; all pages.

LDR Medical, by its attorneys; Reply to Office Action for App. No. 02784881, Pub'n. No. EP1406563; Oct. 14, 2009; EPO; Munich, Germany; all pages.

European Patent Office; Notice of Intent to Grant Patent for App. No. 02784881, Pub'n. No. EP1406563; Aug. 26, 2010; EPO; Munich, Germany; all pages.

European Patent Office; Search Report for Pub'n. No. EP2113228, Application No. EP09009533; Oct. 6, 2009; EPO; Munich, Germany; all pages.

LDR Medical, by its attorneys; Amendment for Pub'n. No. EP2113228, Application No. EP09009533; Apr. 26, 2010; EPO; Munich, Germany; all pages.

European Patent Office; Search Report for Pub'n. No. EP2340788, Application No. EP11157596; Jun. 8, 2011; EPO; Munich, Germany; all pages.

LDR Medical, by its attorneys; Amendment for Pub'n. No. EP1996127, Application No. EP07733892; Nov. 26, 2008; EPO; Munich, Germany; all pages.

National Institute of Industrial Property (France); Search Report for Pub'n. No. FR2897259, App. No. FR0601315; Oct. 11, 2006; National Institute of Industrial Property (France); France; all pages.

World Intellectual Property Organization; International Search Report and Written Opinon of the International Searching Authority for International App. No. PCT/IB2007/000367, PCT Pub'n. No. WO2007093900; Oct. 22, 2007; WIPO; Geneva, Switzerland; all pages.

World Intellectual Property Organization; International Preliminary Report on Patentability for International App. No. PCT/IB2007/000367, PCT Pub'n. No. WO2007093900; Feb. 5, 2008; WIPO; Geneva, Switzerland; all pages.

LDR Medical, by its attorneys; Amendment for Pub'n. No. EP2162098, Application No. EP08762820; Jan. 6, 2010; EPO; Munich, Germany; all pages.

(56) References Cited

OTHER PUBLICATIONS

European Patent Office; Office Action for Pub'n. No. EP2162098, Application No. EP08762820; Jan. 17, 2012; EPO; Munich, Germany; all pages.
LDR Medical, by its attorneys; Reply to Office Action for Pub'n. No. EP2162098, Application No. EP08762820; Jul. 27, 2012; EPO; Munich, Germany; all pages.
National Institute of Industrial Property (France); Search Report for Pub'n. No. FR2916956, App. No. FR0704155; Jan. 30, 2008; National Institute of Industrial Property (France); France; all pages.
World Intellectual Property Organization; International Search Report and Written Opinion of the International Searching Authority for International App. No. PCT/IB2008/001484, PCT Pub'n. No. WO2008149223; Feb. 16, 2009; WIPO; Geneva, Switzerland; all pages.
LDR Medical, by its attorneys; Amendment for International App. No. PCT/IB2008/001484, Pub'n. No. WO2008149223; May 13, 2009; WIPO; Geneva, Switzerland; all pages.
World Intellectual Property Organization; International Preliminary Report on Patentability for International App. No. PCT/IB2008/001484, PCT Pub'n. No. WO2008149223; Aug. 5, 2009; WIPO; Geneva, Switzerland; all pages.
World Intellectual Property Organization; International Search Report and Written Opinion of the International Searching Authority for International App. No. PCT/IB2009/008048, PCT Pub'n. No. WO2011080535; Feb. 2, 2011; WIPO; Geneva, Switzerland; all pages.
LDR Medical, by its attorneys; Demand for International App. No. PCT/IB2009/008048, PCT Pub'n. No. WO2011080535; Apr. 19, 2011; WIPO; Geneva, Switzerland; all pages.
World Intellectual Property Organization; Interview Summary for International App. No. PCT/IB2009/008048, PCT Pub'n. No. WO2011080535; Feb. 14, 2012; WIPO; Geneva, Switzerland; all pages.
LDR Medical, by its attorneys; Amendment for International App. No. PCT/IB2009/008048, Pub'n. No. WO2011080535; Apr. 2, 2012; WIPO; Geneva, Switzerland; all pages.
World Intellectual Property Organization; International Preliminary Report on Patentability for International App. No. PCT/IB2009/008048, PCT Pub'n. No. WO2011080535; Apr. 18, 2012; WIPO; Geneva, Switzerland; all pages.
National Institute of Industrial Property (France); Search Report in Fench Pub. No. FR2987256, App. No. FR1251733; Dec. 5, 2012; National Institute of Industrial Property (France); France; all pages.
World Intellectual Property Organization; International Search Report and Written Opinion of the International Searching Authority for International App. No. PCT/EP2013/053622, PCT Pub'n. No. WO2013124453; May 29, 2013; WIPO; Geneva, Switzerland; all pages.
LDR Medical, by its attorneys; Response to International Search Report for International App. No. PCT/EP2013/053622, International Application No. PCT/EP2013/053622; Dec. 18, 2013; WIPO; Geneva, Switzerland; all pages.
World Intellectual Property Organization; International Preliminary Report on Patentability for International App. No. PCT/EP2013/053622, PCT Pub'n. No. WO 2013/124453; Jul. 11, 2014; WIPO; Geneva, Switzerland; all pages.
European Patent Office; search report in Application No. 10185004, Pub. No. EP2327375; Apr. 6, 2011; European Patent Office; Munich, Germany; All Pages.
European Patent Office; search report in Application No. 13170071, Pub. No. EP2633835; Oct. 1, 2013; European Patent Office; Munich, Germany; All Pages.
National Institute of Industrial Property (France); Preliminary Search Report in Fench Application No. FR0213833, Pub. No. FR2846550; Jul. 10, 2003; National Institute of Industrial Property (France); France; all pages.
World Intellectual Property Organization; International Preliminary Examination Report for International Application No. PCT/IB03/04872, Pub. No. WO2004041129; Mar. 1, 2005; WIPO; Geneva, Switzerland; all pages.
World Intellectual Property Organization; International Search Report in International Application No. PCT/IB03/04872, Pub. No. WO2004041129; Mar. 3, 2004; WIPO; Geneva, Switzerland; all pages.
European Patent Office; Office action and search report in Application No. 05857774, Pub. No. EP1845903; May 6, 2009; European Patent Office; Munich, Germany; All Pages.
LDR Medical, by its attorneys; Amendments and Reply in European Patent Application No. 05857774, Pub. No. EP1845903; Nov. 13, 2009; European Patent Office; Munich, Germany; All Pages.
European Patent Office; Office action and search report in Application No. 05857774, Pub. No. EP1845903; Apr. 11, 2011; European Patent Office; Munich, Germany; All Pages.
LDR Medical, by its attorneys; Amendments and Reply in European Patent Application No. 05857774, Pub. No. EP1845903; Oct. 11, 2011; European Patent Office; Munich, Germany; All Pages.
European Patent Office; Office action and search report in Application No. 11165170, Pub. No. EP2363080; Jul. 21, 2011; European Patent Office; Munich, Germany; All Pages.
LDR Medical, by its attorneys; Amendments and Reply in European Patent Application No. 11165170, Pub. No. EP2363080; Mar. 6, 2012; European Patent Office; Munich, Germany; All Pages.
European Patent Office; Office action in Application No. 11165170, Pub. No. EP2363080; May 15, 2012; European Patent Office; Munich, Germany; All Pages.
National Institute of Industrial Property (France); Search Report for Pub'n. No. FR2879436, App. No. FR0413728; Aug. 11, 2005; National Institute of Industrial Property (France); France; all pages.
World Intellectual Property Organization; International Search Report and Written Opinion of the International Searching Authority for PCT Pub'n No. WO2006120505, App. No. PCT/IB2005/004093; Aug. 31, 2006; WIPO; Geneva, Switzerland; all pages.
LDR Medical, by its attorneys; Chapter II amendments for PCT Pub'n No. WO2006120505, App. No. PCT/IB2005/004093; Oct. 30, 2006; WIPO; Geneva, Switzerland; All Pages.
World Intellectual Property Organization; International Preliminary Report on Patentability for PCT Pub'n No. WO2006120505, App. No. PCT/IB2005/004093; Feb. 22, 2007; WIPO; Geneva, Switzerland; all pages.
U.S. Patent & Trademark Office; Officed Action in U.S. Appl. No. 12/279,664; Sep. 14, 2011; USPTO; Alexandria, Virgina, All Pages.
LDR Medical, by its attorney; Reply to Office Action in U.S. Appl. No. 12/279,664; Mar. 14, 2012; USPTO, Alexandria, Virgina; All Pages.
U.S. Patent & Trademark Office; Notice of Allowance and Interview Summary in U.S. Appl. No. 12/279,664; Apr. 11, 2012; USPTO; Alexandria, Virgina; All Pages.
U.S. Patent & Trademark Office; Notice of Allowance in U.S. Appl. No. 12/279,664; May 29, 2012; USPTO; Alexandria, Virgina; All Pages.
U.S. Patent & Trademark Office; Office Action in U.S. Appl. No. 13/585,063; Nov. 6, 2014; USPTO; Alexandria, Virgina; All Pages.
U.S. Patent & Trademark Office; Office Action in U.S. Appl. No. 12/134,884; Jan. 31, 2012; USPTO; Alexandria, Virgina; All Pages.
LDR Medical, by its attorneys; Reply to Office Action in U.S. Appl. No. 12/134,884; Jul. 31, 2012; USPTO; Alexandria, Virgina; All Pages.
U.S. Patent & Trademark Office; Notice of Allowance in U.S. Appl. No. 12/134,884; Nov. 1, 2012; USPTO; Alexandria, Virgina; All Pages.
U.S. Patent & Trademark Office; Office Action in U.S. Appl. No. 13/732,244; Apr. 30, 2014; USPTO; Alexandria, Virgina; All Pages.
LDR Medical, by its attorney; Reply to Office Action in U.S. Appl. No. 13/732,244; Jul. 30, 2014; USPTO; Alexandria, Virgina; All Pages.
U.S. Patent & Trademark Office; Office Action in U.S. Appl. No. 13/732,244; Sep. 19, 2014; USPTO; Alexandria, Virgina; All Pages.
U.S. Patent & Trademark Office; Office Action in U.S. Appl. No. 13/520,041; Mar. 20, 2014; USPTO; Alexandria, Virgina; All Pages.

(56) References Cited

OTHER PUBLICATIONS

LDR Medical, by its attorneys; Reply to Office Action in U.S. Appl. No. 13/520,041; Sep. 19, 2014; USPTO; Alexandria, Virgina; All Pages.
U.S. Patent & Trademark Office; Office Action in U.S. Appl. No. 13/520,041; Oct. 6, 2014; USPTO; Alexandria, Virgina; All Pages.
U.S. Patent & Trademark Office; Office Action in U.S. Appl. No. 13/538,078; May 12, 2014; USPTO; Alexandria, Virgina; All Pages.
LDR Medical, by its attorneys; Reply to Office Action in U.S. Appl. No. 13/538,078; Oct. 14, 2014; USPTO; Alexandria, Virgina; All Pages.
U.S. Patent & Trademark Office; Notice of Allowance in U.S. Appl. No. 13/538,078; Oct. 20, 2014; USPTO; Alexandria, Virgina; All Pages.
U.S. Patent & Trademark Office; Examiner's Interview Summary in U.S. Appl. No. 13/774,547; Jul. 3, 2014; USPTO; Alexandria, Virgina; All Pages.
U.S. Patent & Trademark Office; Notice of Allowance in U.S. Appl. No. 13/774,547; Jul. 3, 2014; USPTO; Alexandria, Virgina; All Pages.
U.S. Patent & Trademark Office; Notice of Allowance in U.S. Appl. No. 13/774,547; Oct. 16, 2014; USPTO; Alexandria, Virgina; All Pages.
U.S. Patent & Trademark Office; Office Action in U.S. Appl. No. 13/158,761; Oct. 17, 2012; USPTO; Alexandria, Virgina; All Pages.
U.S. Patent & Trademark Office; Examiner's Interview Summary in U.S. Appl. No. 13/158,761; Oct. 21, 2012; USPTO; Alexandria, Virgina; All Pages.
LDR Medical, by its attorneys; Reply to Office Action in U.S. Appl. No. 13/158,761; Nov. 19, 2012; USPTO; Alexandria, Virgina; All Pages.
U.S. Patent & Trademark Office; Office Action in U.S. Appl. No. 13/158,761; Feb. 28, 2013; USPTO; Alexandria, Virgina, All Pages.
LDR Medical, by its attorneys; Reply to Office Action in U.S. Appl. No. 13/158,761; Jul. 29, 2013; USPTO; Alexandria, Virgina; All Pages.
U.S. Patent & Trademark Office; Examiner's Interview Summary in U.S. Appl. No. 13/158,761; Aug. 1, 2013; USPTAO; Alexandria, Virgina; All Pages.
U.S. Patent & Trademark Office; Office Action in U.S. Appl. No. 13/158,761; Aug. 14, 2013; USPTO; Alexandria, Virgina; All Pages.
LDR Medical, by its attorneys; Request for Continued Examiniation in U.S. Appl. No. 13/158,761; Nov. 14, 2013; USPTO; Alexandria, Virgina; All Pages.
U.S. Patent & Trademark Office; Office Action in U.S. Appl. No. 13/158,761; Oct. 22, 2014; USPTO; Alexandria, Virgina; All Pages.
U.S. Patent & Trademark Office; Notice of Allowance in U.S. Appl. No. 11/109,276; Dec. 8, 2009; USPTO; Alexandria, Virgina; All Pages.
LDR Medical, by its attorneys; Reply to Office Action in U.S. Appl. No. 11/109,276; Aug. 4, 2009; USPTO; Alexandria, Virgina; All Pages.
U.S. Patent & Trademark Office; Office Action in U.S. Appl. No. 11/109,276; Feb. 13, 2009; USPTO; Alexandria, Virgina; All Pages.
LDR Medical, by its attorneys; Reply to Office Action in U.S. Appl. No. 11/109,276; Jan. 26, 2009; USPTO; Alexandria, Virgina; All Pages.
U.S. Patent & Trademark Office; Office Action in U.S. Appl. No. 11/109,276; Jul. 24, 2008; USPTO; Alexandria, Virgina; All Pages.
LDR Medical, by its attorneys; Reply to Office Action in U.S. Appl. No. 11/109,276; Apr. 16, 2008; USPTO; Alexandria, Virgina; All Pages.
U.S. Patent & Trademark Office; Office Action in U.S. Appl. No. 11/109,276; Oct. 16, 2007; USPTO; Alexandria, Virgina; All Pages.
LDR Medical, by its attorneys; Reply to Office Action in U.S. Appl. No. 11/109,276; Aug. 6, 2007; USPTO; Alexandria, Virgina; All Pages.
U.S. Patent & Trademark Office; Office Action in U.S. Appl. No. 11/109,276; Feb. 6, 2007; USPTO; Alexandria, Virgina; All Pages.
U.S. Patent & Trademark Office; Notice of Allowance in U.S. Appl. No. 12/360,050; Aug. 2, 2012; USPTO; Alexandria, Virgina; All Pages.
U.S. Patent & Trademark Office; Notice of Allowance in U.S. Appl. No. 12/360,050; Jul. 6, 2012; USPTO; Alexandria, Virgina; All Pages.
U.S. Patent & Trademark Office; Notice of Allowance in U.S. Appl. No. 12/360,050; May 18, 2012; USPTO; Alexandria, Virgina; All Pages.
U.S. Patent & Trademark Office; Notice of Allowance in U.S. Appl. No. 12/360,050; Mar. 26, 2012; USPTO; Alexandria, Virgina; All Pages.
LDR Medical, by its attorneys; Reply to Office Action in U.S. Appl. No. 12/360,050; Mar. 6, 2012; USPTO; Alexandria, Virgina; All Pages.
U.S. Patent & Trademark Office; Office Action in U.S. Appl. No. 12/360,050; Sep. 6, 2011; USPTO; Alexandria, Virgina; All Pages.
LDR Medical, by its attorneys; Reply to Office Action in U.S. Appl. No. 12/360,050; Jun. 16, 2011; USPTO; Alexandria, Virgina; All Pages.
U.S. Patent & Trademark Office; Office Action in U.S. Appl. No. 12/360,050; Dec. 17, 2010; USPTO; Alexandria, Virgina; All Pages.
U.S. Patent & Trademark Office; Office Action in U.S. Appl. No. 13/603,043; Jul. 24, 2014; USPTO; Alexandria, Virgina; All Pages.
LDR Medical, by its attorneys; Reply to Office Action in U.S. Appl. No. 13/603,043; May 21, 2014; USPTO; Alexandria, Virgina; All Pages.
U.S. Patent & Trademark Office; Office Action in U.S. Appl. No. 13/603,043; Nov. 21, 2013; USPTO; Alexandria, Virgina; All Pages.
LDR Medical, by its attorneys; Reply to Office Action in U.S. Appl. No. 13/603,043; Oct. 9, 2013; USPTO; Alexandria, Virgina; All Pages.
U.S. Patent & Trademark Office; Office Action in U.S. Appl. No. 13/603,043; Apr. 9, 2013; USPTO; Alexandria, Virgina; All Pages.
U.S. Patent & Trademark Office; Notice of Allowance in U.S. Appl. No. 10/533,846; Nov. 4, 2009; USPTO; Alexandria, Virgina; All Pages.
LDR Medical, by its attorneys; Reply to Office Action in U.S. Appl. No. 10/533,846; Apr 15, 2009; USPTO; Alexandria, Virgina; All Pages.
U.S. Patent & Trademark Office; Office Action in U.S. Appl. No. 10/533,846; Oct. 15, 2008; USPTO; Alexandria, Virgina; All Pages.
LDR Medical, by its attorneys; Reply to Office Action in U.S. Appl. No. 10/533,846; Jun. 25, 2008; USPTO; Alexandria, Virgina; All Pages.
U.S. Patent & Trademark Office; Office Action in U.S. Appl. No. 10/533,846; Dec. 26, 2007; USPTO; Alexandria, Virgina; All Pages.
LDR Medical, by its attorneys; Reply to Office Action in U.S. Appl. No. 10/533,846; Oct. 16, 2007; USPTO; Alexandria, Virgina; All Pages.
U.S. Patent & Trademark Office; Office Action in U.S. Appl. No. 10/533,846; Apr. 18, 2007; USPTO; Alexandria, Virgina; All Pages.
U.S. Patent & Trademark Office; Notice of Allowance in U.S. Appl. No. 12/424,364; Aug. 2, 2012; USPTO; Alexandria, Virgina; All Pages.
U.S. Patent & Trademark Office; Notice of Allowance in U.S. Appl. No. 12/424,364; Jul. 24, 2012; USPTO; Alexandria, Virgina; All Pages.
LDR Medical, by its attorneys; Reply to Office Action in U.S. Appl. No. 12/424,364; Jul. 6, 2012; USPTO; Alexandria, Virgina; All Pages.
U.S. Patent & Trademark Office; Office Action in U.S. Appl. No. 12/424,364; May 23, 2012; USPTO; Alexandria, Virgina; All Pages.
LDR Medical, by its attorneys; Interview Summary and Terminal Disclaimer in U.S. Appl. No. 12/424,364; May 22, 2012; USPTO; Alexandria, Virgina; All Pages.
LDR Medical, by its attorneys; Reply to Office Action in U.S. Appl. No. 12/424,364; Feb. 27, 2012; USPTO; Alexandria, Virgina; All Pages.
U.S. Patent & Trademark Office; Office Action in U.S. Appl. No. 12/424,364; Jan. 26, 2012; USPTO; Alexandria, Virgina; All Pages.

(56) References Cited

OTHER PUBLICATIONS

LDR Medical, by its attorneys; Reply to Office Action in U.S. Appl. No. 12/424,364; Nov. 18, 2011; USPTO; Alexandria, Virgina; All Pages.
U.S. Patent & Trademark Office; Office Action in U.S. Appl. No. 12/424,364; May 18, 2011; USPTO; Alexandria, Virgina; All Pages.
U.S. Patent & Trademark Office; Notice of Allowance in U.S. Appl. No. 13/616,448; Feb. 7, 2014; USPTO; Alexandria, Virgina; All Pages.
U.S. Patent & Trademark Office; Office Action in U.S. Appl. No. 13/616,448; Aug. 22, 2013; USPTO; Alexandria, Virgina; All Pages.
U.S. Patent & Trademark Office; Office Action in U.S. Appl. No. 14/306,785; Oct. 22, 2014; USPTO; Alexandria, Virgina; All Pages.
U.S. Patent & Trademark Office; Office Action in U.S. Appl. No. 10/276,712; Jun. 30, 2004; USPTO; Alexandria, Virgina; All Pages.
LDR Medical, by its attorneys; Reply to Office Action in U.S. Appl. No. 10/276,712; Sep. 27, 2004; USPTO; Alexandria, Virgina; All Pages.
U.S. Patent & Trademark Office; Office Action in U.S. Appl. No. 10/276,712; Dec. 23, 2004; USPTO; Alexandria, Virgina; All Pages.
LDR Medical, by its attorneys; Reply to Office Action in U.S. Appl. No. 10/276,712; Mar. 1, 2005; USPTO; Alexandria, Virgina; All Pages.
U.S. Patent & Trademark Office; Office Action in U.S. Appl. No. 10/276,712; May 27, 2005; USPTO; Alexandria, Virgina; All Pages.
LDR Medical, by its attorneys; Reply to Office Action in U.S. Appl. No. 10/276,712; Aug. 29, 2005; USPTO; Alexandria, Virgina; All Pages.
U.S. Patent & Trademark Office; Office Action in U.S. Appl. No. 10/276,212; Nov. 14, 2005; USPTO; Alexandria, Virgina; All Pages.
LDR Medical, by its attorneys; Reply to Office Action in U.S. Appl. No. 10/276,712; Jan. 17, 2006; USPTO; Alexandria, Virgina; All Pages.
U.S. Patent & Trademark Office; Office Action in U.S. Appl. No. 10/276,712; Feb. 8, 2006; USPTO; Alexandria, Virgina; All Pages.
LDR Medical, by its attorneys; Reply to Office Action in U.S. Appl. No. 10/276,712; Mar. 14, 2006; USPTO; Alexandria, Virgina; All Pages.
U.S. Patent & Trademark Office; Office Action in U.S. Appl. No. 10/276,712; Jun. 7, 2006; USPTO; Alexandria, Virgina; All Pages.
LDR Medical, by its attorneys; Reply to Office Action in U.S. Appl. No. 10/276,712; Oct. 6, 2006; USPTO; Alexandria, Virgina; All Pages.
U.S. Patent & Trademark Office; Office Action in U.S. Appl. No. 10/276,712; Dec. 20, 2006; USPTO; Alexandria, Virgina; All Pages.
LDR Medical, by its attorneys; Reply to Office Action in U.S. Appl. No. 10/276,712; Jun. 19, 2007; USPTO; Alexandria, Virgina; All Pages.
U.S. Patent & Trademark Office; Notice of Allowance in U.S. Appl. No. 10/276,712; Jul. 30, 2007; USPTO; Alexandria, Virgina; All Pages.
U.S. Patent & Trademark Office; Office Action in U.S. Appl. No. 11/767,386; Dec. 24, 2009; USPTO; Alexandria, Virgina; All Pages.
LDR Medical, by its attorneys; Reply to Office Action in U.S. Appl. No. 11/767,386; Apr. 26, 2010; USPTO; Alexandria, Virgina; All Pages.
U.S. Patent & Trademark Office; Office Action in U.S. Appl. No. 11/767,386; Jul. 21, 2010; USPTO; Alexandria, Virgina; All Pages.
LDR Medical, by its attorneys; Reply to Office Action in U.S. Appl. No. 11/767,386; Jan. 21, 2011; USPTO; Alexandria, Virgina; All Pages.
U.S. Patent & Trademark Office; Office Action in U.S. Appl. No. 11/767,386; Mar. 24, 2011; USPTO; Alexandria, Virgina; All Pages.
LDR Medical, by its attorneys; Reply to Office Action in U.S. Appl. No. 11/767,386; Sep. 26, 2011; USPTO; Alexandria, Virgina; All Pages.
U.S. Patent & Trademark Office; Office Action in U.S. Appl. No. 11/767,386; Apr. 24, 2013; USPTO; Alexandria, Virgina; All Pages.
LDR Medical, by its attorneys; Reply to Office Action in U.S. Appl. No. 11/767,386; Jul. 24, 2013; USPTO; Alexandria, Virgina; All Pages.
U.S. Patent & Trademark Office; Notice of Allowance in U.S. Appl. No. 11/767,386; Aug. 30, 2013; USPTO: Alexandria, Virgina; All Pages.
LDR Medical, by its attorneys; Response to Statement of Reasons for Allowance in U.S. Appl. No. 11/767,386; Dec. 2, 2013; USPTO; Alexandria, Virgina; All Pages.
U.S. Patent & Trademark Office; Restriction Requirement in U.S. Appl. No. 11/378,165; Sep. 28, 2007; USPTO; Alexandria, Virgina; All Pages.
LDR Medical, by its attorneys; Reply to Restriction Requirement in U.S. Appl. No. 11/378,165; Feb. 28, 2008; USPTO; Alexandria, Virgina; All Pages.
U.S. Patent & Trademark Office; Office Action in U.S. Appl. No. 11/378,165; May 27, 2008; USPTO; Alexandria, Virgina; All Pages.
LDR Medical, by its attorneys; Reply to Office Action in U.S. Appl. No. 11/378,165; Nov. 26, 2008; USPTO; Alexandria, Virgina; All Pages.
U.S. Patent & Trademark Office; Office Action in U.S. Appl. No. 11/378,165; Feb. 17, 2009; USPTO; Alexandria, Virgina; All Pages.
LDR Medical, by its attorneys; Reply to Office Action in U.S. Appl. No. 11/378,165; Aug. 4, 2009; USPTO; Alexandria, Virgina; All Pages.
U.S. Patent & Trademark Office; Office Action in U.S. Appl. No. 11/378,165; Aug. 11, 2009; USPTO; Alexandria, Virgina; All Pages.
LDR Medical, by its attorneys; Request for Continued Examination in U.S. Appl. No. 11/378,165; Aug. 14, 2009; USPTO; Alexandria, Virgina; All Pages.
U.S. Patent & Trademark Office; Office Action in U.S. Appl. No. 11/378,165; Oct. 26, 2009; USPTO; Alexandria, Virgina; All Pages.
LDR Medical, by its attorneys; Reply to Office Action in U.S. Appl. No. 11/378,165, Apr. 26, 2010; USPTO; Alexandria, Virgina; All Pages.
U.S. Patent & Trademark Office; Examiner's Interview Summary in U.S. Appl. No. 11/378,165; May 20, 2010; USPTO; Alexandria, Virgina; All Pages.
LDR Medical, by its attorneys; Applicant's Interview Summary in U.S. Appl. No. 11/378,165; June. 18, 2010; USPTO; Alexandria, Virgina; All Pages.
U.S. Patent & Trademark Office; Office Action in U.S. Appl. No. 11/378,165; Sep. 24, 2010; USPTO; Alexandria, Virgina; All Pages.
LDR Medical, by its attorneys; Reply to Office Action in U.S. Appl. No. 11/378,165; Mar. 24, 2011; USPTO; Alexandria, Virgina; All Pages.
U.S. Patent & Trademark Office; Office Action in U.S. Appl. No. 11/378,165; Jun. 4, 2012; USPTO; Alexandria, Virgina; All Pages.
LDR Medical, by its attorneys; Reply to Office Action in U.S. Appl. No. 11/378,165; Nov. 5, 2012; USPTO; Alexandria, Virgina; All Pages.
U.S. Patent & Trademark Office; Notice of Allowance in U.S. Appl. No. 11/378,165; Nov. 26, 2012; USPTO; Alexandria, Virgina; All Pages.
U.S. Patent & Trademark Office; Examiner's Interview Summary in U.S. Appl. No. 11/378,165; Nov. 26, 2012; USPTO; Alexandria, Virgina; All Pages.
LDR Medical, by its attorneys; Response to Statement of Reasons for Allowance in U.S. Appl. No. 11/378,165; Feb. 26, 2013; USPTO; Alexandria, Virgina; All Pages.
U.S. Patent & Trademark Office; Office Action in U.S. Appl. No. 13/854,808; Apr. 18, 2014; USPTO; Alexandria, Virgina; All Pages.
LDR Medical, by its attorneys; Reply to Office Action in U.S. Appl. No. 13/854,808; Jun. 18,2014; USPTO; Alexandria, Virgina; All Pages.
U.S. Patent & Trademark Office; Office Action in U.S. Appl. No. 13/854,808; Jul. 7, 2014; USPTO; Alexandria, Virgina; All Pages.

\* cited by examiner

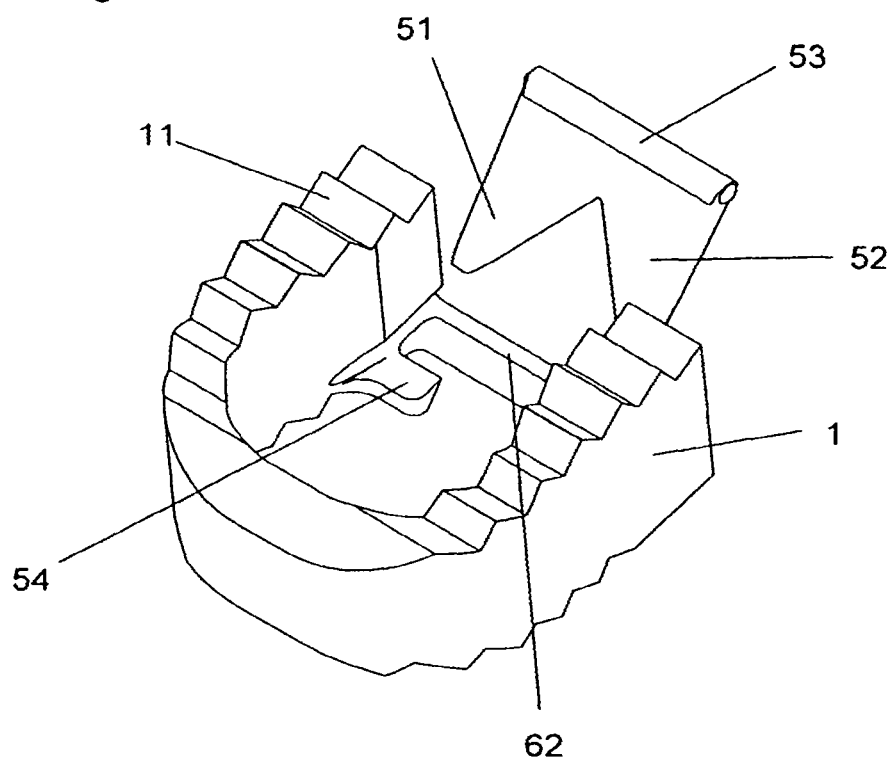

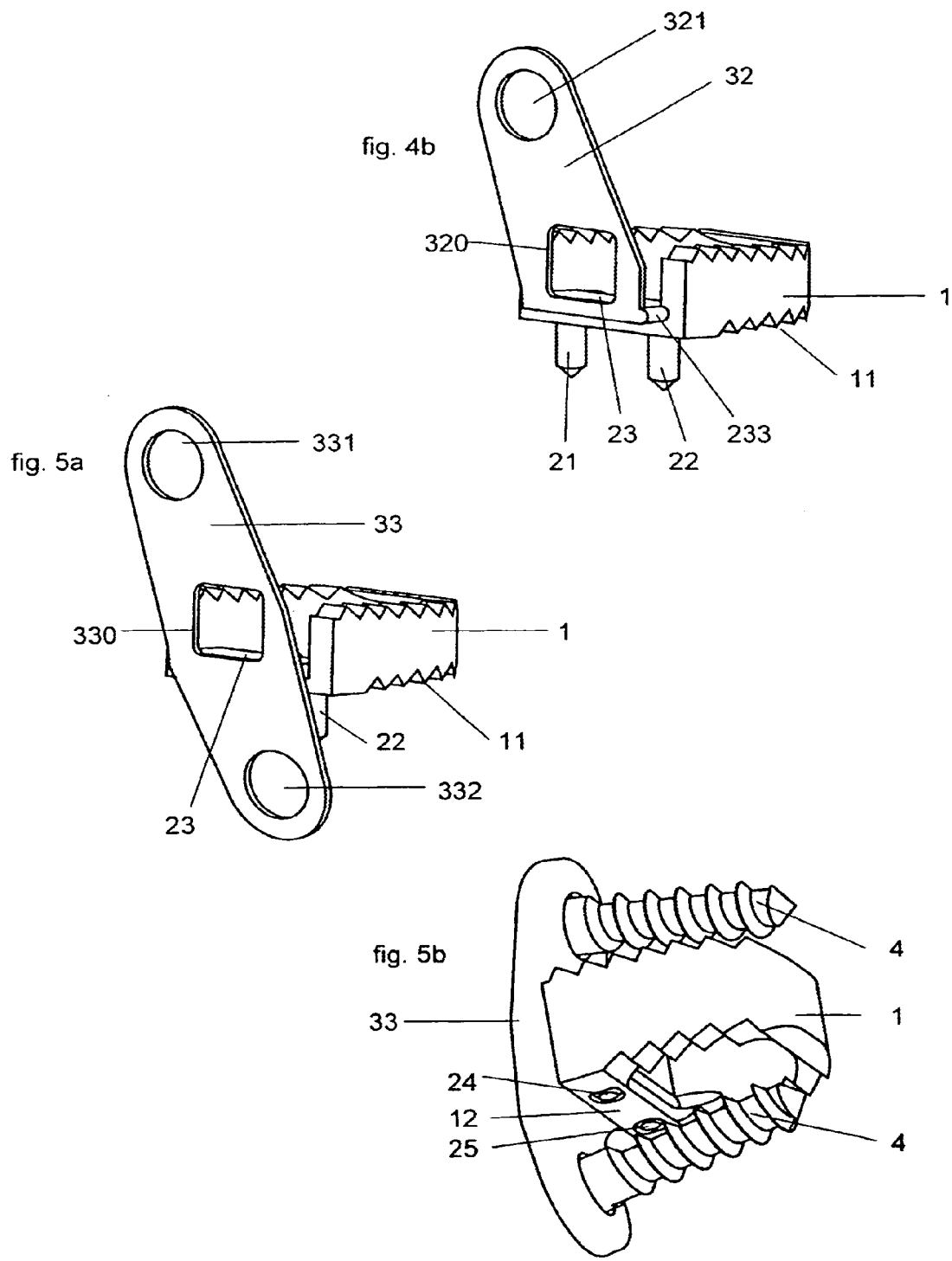

VERTEBRAL CAGE DEVICE WITH MODULAR FIXATION

CROSS-REFERENCE TO RELATED APPLICATIONS

This application is a continuation of U.S. patent application Ser. No. 12/430,768, filed Apr. 27, 2009, which is a continuation of U.S. patent application Ser. No. 10/483,563, filed May 21, 2004, and issuing Sep. 29, 2009, as U.S. Pat. No. 7,594,931, which claims priority to International Application PCT/IB02/03390, filed Jul. 12, 2002, which claims priority to French Patent Application No. 01/09381, filed Jul. 13, 2001.

BACKGROUND

The present invention concerns an arthrodesis device, used to enable fusing of two contiguous vertebrae by development of bony tissues with replacement of fibrocartilaginous discs ensuring the bonding between the vertebrae of the vertebral column or the end of the latter.

The intervertebral discs are formed from a deformable but not compressible part called "nucleus pulposus" containing approximately 80% water, surrounded by several elastic fibrous layers uniting to maintain the nucleus, absorbing part of the forces applied to the disc unit, and stabilizing the articulation. These parts may often be degraded by compression, displacement or wear and tear, following shocks, infections, exaggerated forces or simply over time. The degradation of this articulation part may cause intense pain in the patient and significant discomfort.

SUMMARY

In a good number of cases, the treatment consists of removing all or part of the damaged intervertebral disc and connecting the vertebrae concerned by causing bony fusion between them. To do that, one places between the vertebrae an artificial structure allowing their separation to be maintained, while with it introducing into the intervertebral space either a bony graft or a bony substitute, compounded material that will be invaded by the growth of adjacent bony tissues. This structure often takes the shape of an open or closed ring called cage, and may be positioned on the basis of a cage by the intervertebral space in the case of cervical vertebrae, or on the basis of one or two cages by the intervertebral space in the case of lumbar vertebrae. This positioning is done most often by the anterior surface of the vertebrae in the case of a cervical cage, or by the anterolateral surface of the vertebrae (one cage) or posterior (two cages) of vertebrae in the case of a lumbar cage. As for grafts and bony substitutes, they are introduced in the cage either before or after its positioning and are therefore found in contact with the two vertebrae surrounding the treated intervertebral space.

During the time necessary for growth and up to the reinforcement of arthrodesis, which may be on the order of six months, it is important that the various movements of forces taking place in the intervertebral space do not cause displacement of the cage, which would then risk deteriorating the bony tissues during formation or even escaping outside this space and damaging the adjacent organs.

To avoid such displacements, a solution used consists of equipping the surfaces of the cage in contact with the vertebrae with varieties of shape such as saw tooth notches as described in the patents FR0006351 or FR2733413. Such a solution however proves to be insufficient in a certain number of cases.

Another solution consists of equipping the cage with a flange that extends on the outside of the intervertebral space and is applied on the side of each of the two contiguous vertebrae, to which it is fixed by a bone anchoring screw. Such a solution has been used since about 1988 and is described for example in the patent FR 2 747 034. Such a plate however represents an overcrowding outside the intervertebral space that sometimes may pose problems in particular in the case of arthrodesis of the cervical vertebrae where the space available is very limited. In fact, the presence of the plate may for example form a daily discomfort for the patient or form an immediate or future obstacle in the positioning of another cage with plate in one of the immediately adjacent plates.

Furthermore, in particular in the case of cervical vertebrae, the movements of the spine often have the tendency to cause loosening of the bone anchoring screws, which decreases the effectiveness of such a plate and may also cause damages to the organs surrounding the plate.

Therefore, it is worthwhile to also provide for a system enabling fixation of the cage without a part extending outside the intervertebral space.

Moreover, these different solutions may fulfil the needs of an arthrodesis operation differently without it being necessarily possible to know in advance which will be preferable. Therefore, it is easier and less expensive to provide for a modular device comprising interchangeable parts for achieving different solutions.

To remedy some of these drawbacks, the present invention proposes an intervertebral arthrodesis device designed to be inserted in an intervertebral space separating the opposite plates of the two adjacent vertebrae, characterised in that it comprises at least one structure called intervertebral cage presenting the shape of a ring that may or may not be open, in which at least one part, along the axis of the spine, has a lower height than the rest of this same cage and forms a small bar crossed by at least one drilling of the axis approximately perpendicular to the plate of at least one of the adjacent vertebrae.

According to one characteristic, the device includes at least one intervertebral cage having on its surfaces in contact with the vertebrae, undulations in shape limiting its possibilities for sliding in a plane parallel to said vertebrae.

According to one characteristic, the device comprises at least one fixation structure for fixedly mounting the cage(s) to at least one of these vertebrae. The fixation structure can be added to at least one intervertebral cage by insertion of a projecting part in at least one bore or opening of the cage.

According to one characteristic, the fixation structure includes at least two bone anchoring pins with approximately parallel axes. The pins are connected together by a small rod, and extend through openings or bores of the small rod of the cages. The pins extending through the opening are pushed into a face of at least one vertebra to keep the cage in position in the intervertebral space.

According to one characteristic, at least one of the bone anchoring pins of the fixation structure includes reliefs for limiting the possibilities of the cage sliding outside the face where it is impacted.

According to one characteristic, the fixation structure comprises at least one fixation plate fixed to the external surface of at least one vertebra and including at least one opening or bore for receiving a bone anchoring screw fixed to this same vertebra.

According to one characteristic, at least one of the openings of the fixation plate presents in the plane of this plate a section at the level of its opening opposite the vertebra that is not as high as in its part located within the thickness of the plate. A bone anchoring screw has a head which presents at least one part of a section greater than that of the opening of the plate and is thus retained within this same opening by this same external opening.

According to one feature, the fixation structure includes at least two locking studs with approximately parallel axes connected by a small rod. These locking studs are inserted into at least one hole or bore of at least one intervertebral cage to lock said fixation structure to said cage and to keep the cage in position in the intervertebral space.

According to one feature, at least one of the ends of the small rod has at least one protuberance clipped in at least one housing arranged in the wall of the intervertebral cage so as to limit or prevent the movements of this same rod relative to this same cage.

According to one characteristic, the fixation structure comprises a fixation plate (called a hemiplate) coupled to the exterior surface of at least one vertebra. The fixation plate structure includes at least one opening or bore through which is inserted a bone anchoring screw fixed in other vertebra to keep said cage in position in the intervertebral space.

According to one feature, the fixation hemiplate with the small rod connecting the anchoring pins or the locking studs forms a piece with an "L" section.

According to one characteristic, the fixation structure comprises a fixation plate (called complete) coupled to the exterior surface of at least two vertebrae. Near each end of the plate there is at least one bore or opening through which is inserted a bone anchoring screw that is fixed in said vertebrae to prevent any migration of the intervertebral cage within or outside the intervertebral space.

According to one characteristic, the complete fixation plate with the small rod connects the anchoring pins or the locking studs with a "T" section.

According to one feature, the fixation plate includes an opening at the level of the intervertebral space. This opening enables the introduction or packing of a graft or bone substitute in the intervertebral space after insertion of the device.

According to one characteristic, each bore in the fixation structure acts with a bone anchoring screw. When the anchoring screw is in place, it is located in a position shifted relative to a plane containing the axis of the spine.

According to one feature, at least one intervertebral cage has, along the axis of the spine, a nonuniform height. This variation in height induces a determined angle between the vertebra faces with respect to the adjacent vertebrae.

According to one characteristic, at least one of the constitutive parts of the device is made from a radiotransparent material.

The invention, with its characteristics and advantages, will be more clearly evident with the reading of the description made in reference to the fixed drawings which:

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3c is a perspective view of a device according to a preferred embodiment of the invention before impacting tongues in an embodiment, where the fixation device comprises anchoring tongues;

FIG. 4b is a perspective view of a device according to a preferred embodiment of the invention where the fixation device comprises anchoring pins and a top hemiplate with an opening;

FIG. 5a is a perspective view of a device according to a preferred embodiment of the invention where the fixation device comprises anchoring pins and a complete plate with an opening; and FIG. 5b is a perspective view of a device according to a preferred embodiment of the invention where the fixation device comprises a complete plate added by locking studs, illustrated with anchoring screws.

DETAILED DESCRIPTION

Reference is now made to the Figures wherein is illustrated ring shaped intervertebral cage (1), designed to be inserted in the intervertebral space (E) to be treated between two contiguous vertebrae, and to be received into an interior cavity (10, FIG. 2a) a bony material acting as a graft, or any structure that can act as a bony substitute or be "assembled" by a growth of bony material. The cavity of the intervertebral cage can thus be filled before or after it is positioned in the intervertebral space.

According to some applications, the device includes a single intervertebral cage (1, FIGS. 1 and 2a), for example to carry out arthrodesis between two cervical vertebrae. It is to be understood that for other applications, the device can include two intervertebral cages (not represented), for example, to carry out arthrodesis between two lumbar vertebrae during positioning by the posterior route.

According to the applications, an intervertebral cage according to the invention may be made in the shape of a closed ring (1, FIG. 3a) or in the form of a ring opened on one side (not represented).

Figure 1A:
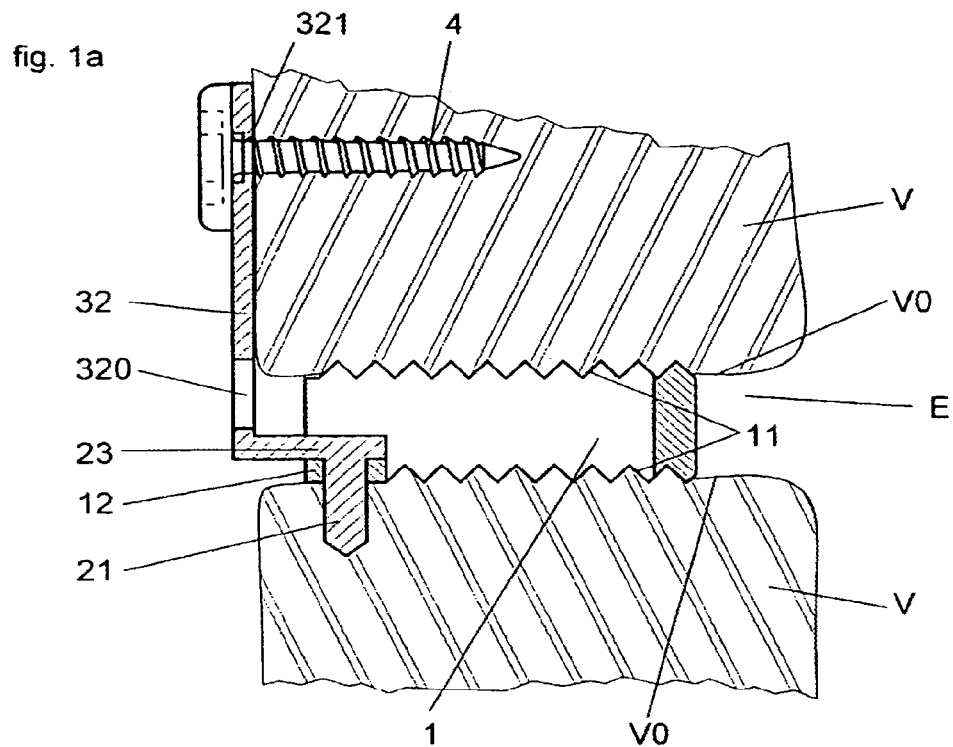
FIG. 1a is a side sectional view of the device according to the invention in an embodiment where the fixation device comprises anchoring pins and a top hemiplate.
Figure 1B:
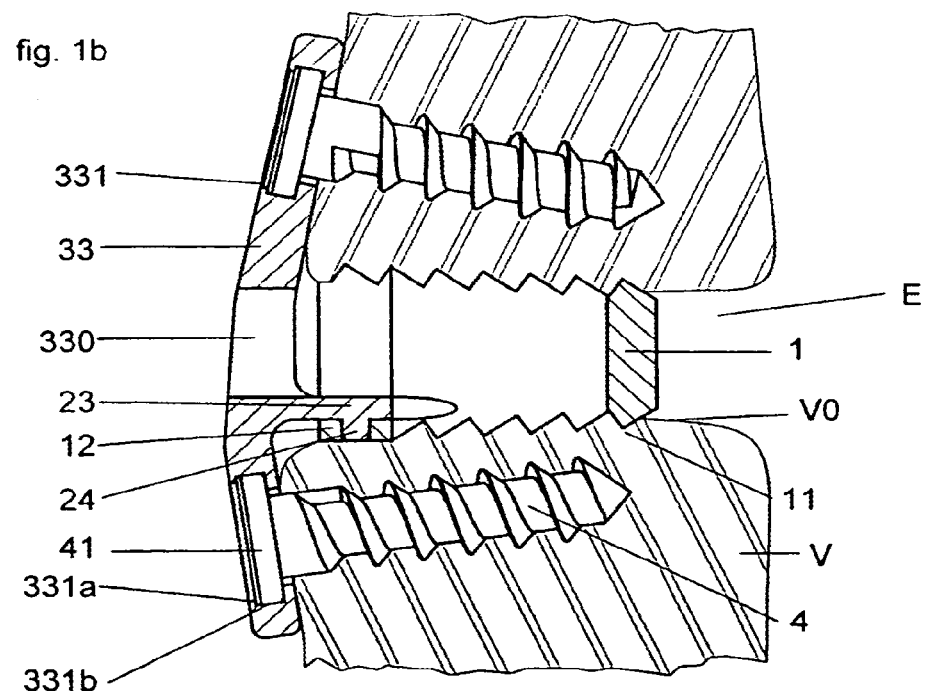
FIG. 1b is a side sectional view of the device according to the invention in an embodiment where the fixation device comprises a complete plate, with opening, added by locking studs and with anchoring screws retained in the openings or bores of the plate.
Figure 2A:
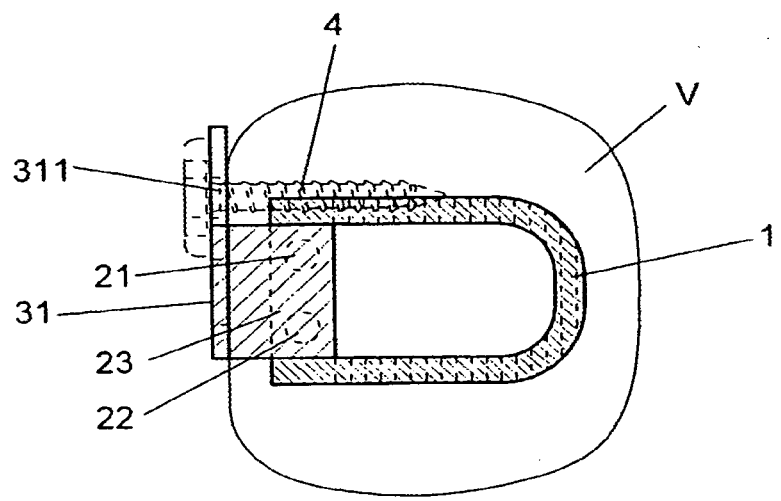
FIG. 2a is a top sectional view of the device according to the invention in an embodiment where the fixation device comprises anchoring pins and a low hemiplate.

In one embodiment represented in FIGS. 1 and 2a, the invention comprises a fixation device enabling its anchoring in the plate (V0) of a vertebra (V) within the intervertebral space (E) to be treated. This fixation device is formed from two anchoring pins (21, 22), with approximately parallel axes and connected by a small rod (23). These anchoring pins are introduced into two drillings (121, 122) made in a thinned down part of the intervertebral cage, then are impacted, that is pushed in with force, into the bony material forming the plate of one of the two vertebrae surrounding the intervertebral space to be treated.

In one embodiment, the thinned down part of the cage forms a small flat rod (12) that abuts small flat rod (23), connecting the two anchoring pins (21, 22) when the latter are impacted in face (V0) of a vertebra (V). The thickness of the small rod (23) connecting the anchoring pins and the small rod (12) formed by a thinning of the intervertebral cage (1) are such that the superimposition of the two small rods (12, 23) after impacting is no higher along the axis of the spine than the rest of the intervertebral cage (1).

Figure 3A:
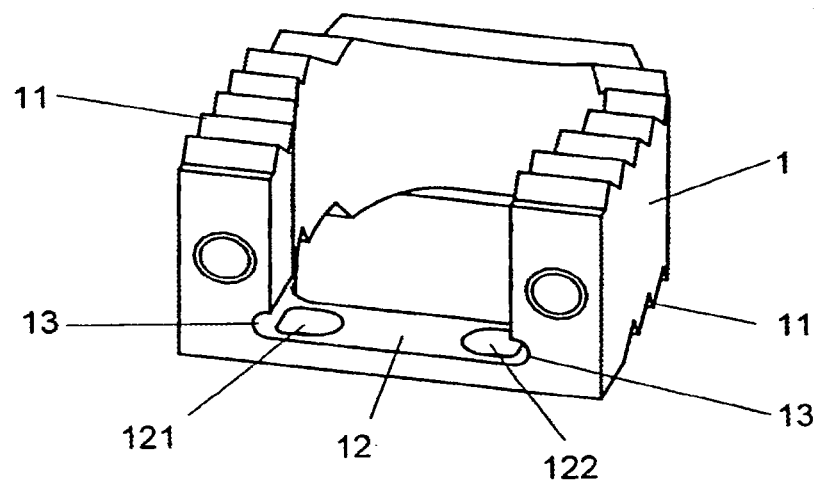
FIG. 3a is a perspective view of an intervertebral cage according to a preferred embodiment of the invention.
Figure 3B:
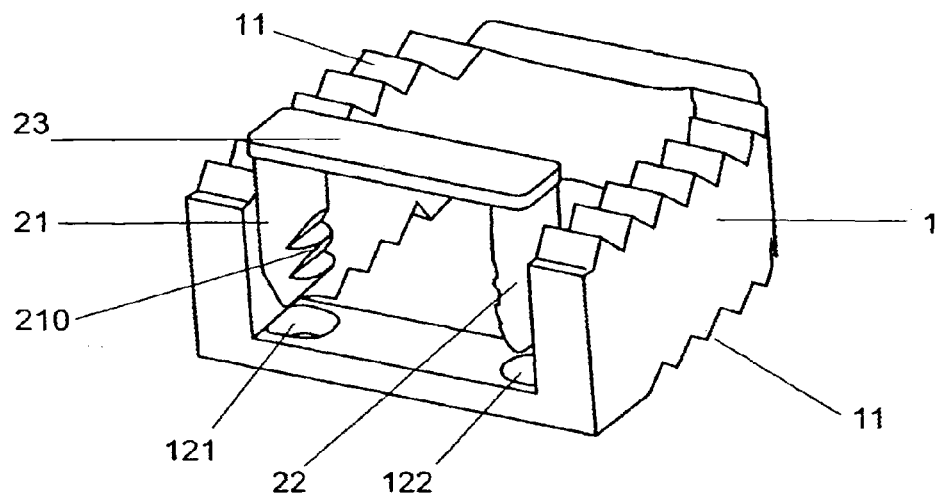
FIG. 3b is a perspective view of a device according to a preferred embodiment of the invention before insertion of impacting pins in an embodiment where the fixation device comprises anchoring pins with undulations in shape.

In one embodiment represented in FIG. 3b the length of the anchoring pins (21, 22) and the thickness of the small rod (23) connecting them are determined so that the sum of these two dimensions forming the height of the fixation device in this embodiment is no greater than the height along the axis of the spine of the rest of the intervertebral cage (1). Thus, it is possible to introduce into this intervertebral space an intervertebral cage already provided with anchoring pins, the latter then only having been impacted into the face (VO) of a vertebra (V), for example with the aid of a spreader, a distractor or another tool of known type.

In one embodiment represented in FIG. 3c, the fixation device, enabling the device to be anchored in the face (V0) of a vertebra (V) within the intervertebral space (E) to be treated, is constituted of an anchoring tongue including legs (51, 52) having intersecting edges forming a "V" are connected by a small rod (53). Legs (51, 52) are introduced between a thinned down part of the intervertebral cage formed by a small rod (62) and two lugs (only one, 54, is represented on FIG. 3c) formed on the device and symmetrically disposed in relation to the device axis. The "V" shaped tongue includes legs (51, 52) is then forced into place similarly to the device provided with pins (21, 22). Legs (51, 52) are forced into place in face V0 of vertebra V so the small flat rod (53), connecting the anchoring legs (51, 52) abuts small flat rod (62). The diameters of the small rod (53) connecting the anchoring tongues and the small rod (62) formed by a thinning of the intervertebral cage (1) are such that the superimposition of the two small rods (62, 53) after legs (51, 52) are forced into face (V0) is no higher along the axis of the spine than the rest of the intervertebral cage (1).

In one embodiment (not shown), the device according to the invention comprises two intervertebral cages. Each of the two cages is formed from an open ring having at least one part having a reduced height along the axis of the spinal cord. In one embodiment, at least one of the cages is in the shape of a "U" or "C" (not shown). Each cage includes at its end a small rod from one part having a reduced height along the axis of the spine. These small rods are crossed by at least one bore or opening having an axis approximately perpendicular to the face (V0) of the vertebra (V) with which they are in contact. In one embodiment, two intervertebral cages are arranged in the intervertebral space with their openings facing each other. At least one fixation device including two anchoring pins with parallel axes connected by a small rod is introduced into the bore of each of the two small rods with ends facing each other. The anchoring pins are then forced into the face of the vertebra and inserted into the bores of the small rods of the intervertebral cages to help to keep said cages immovable.

In one embodiment, an intervertebral cage (1) used in a device according to the invention has at least one undulating surface (11) in contact with the vertebrae; in one example, the undulating contact surface (11) has a saw tooth shape as illustrated in FIG. 3c. Under the pressure exerted by the vertebrae surrounding the treated intervertebral space (E), the undulating surface (11) supports the surface of faces (V0) of these same vertebrae to limit the risks of displacement of the intervertebral cage.

In one embodiment, represented in FIGS. 1, 2a and 4b, a fixation device comprises a plate called top hemiplate (32) united with the small rod (23) connecting the anchoring pins (21, 22) to each other. Hemiplate (32) extends outside the intervertebral space (E) to be treated and is coupled to the exterior surface of the vertebra opposite the vertebra receiving the anchoring pins. This top hemiplate (32) includes at least one bore or opening (321) which receives a bone anchoring screw (4) of a known type. Screw (4) is fixed in the body of the vertebra and inserted in the face (V0) to prevent any migration of the intervertebral cage (1) within or outside the treated intervertebral space (E). Top hemiplate (32) also comprises an opening (320) enabling introduction of the graft into the cage (1) after the cage is positioned in the intervertebral space. The part of the piece connecting the small rod (23) and the top hemiplate (32) has an "L" shape.

Figure 4A:
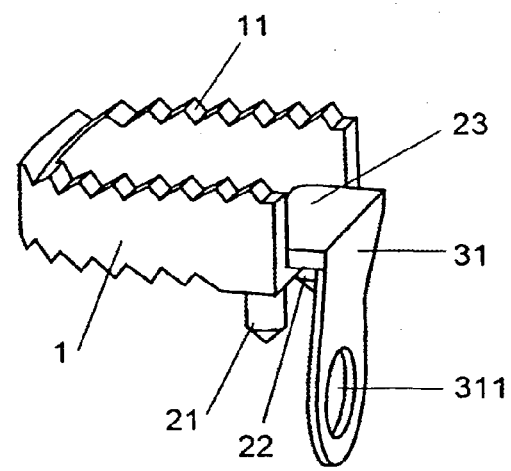
FIG. 4a is a perspective view of a device according to a preferred embodiment of the invention where the fixation device comprises anchoring pins and a low hemiplate.

In one embodiment represented in FIG. 4a, a plate called bottom hemiplate (31), is fixed in the same way to the vertebra receiving the anchoring pins. The part of the piece connecting the small rod (23) and the bottom hemiplate (31) has an "L" shape.

In one embodiment represented in FIG. 5a, a fixation device comprises a plate called complete plate (33) that is integral with the small rod (23) connecting the anchoring pins (21, 22) to each other. Plate (33) extends to the exterior of the intervertebral space (E) to be treated and is coupled to the exterior surface of these two vertebrae surrounding the intervertebral space (E) to be treated. The part of the piece connecting the small rod (23) and the complete plate (33) has a "T" shape. Complete plate (33) includes at least two bores (331, 332), each of which receives a bone anchoring screw (4) of a known type. Screw (4) is fixed in the body of the corresponding vertebra and inserted in the plate (33) to prevent any migration of the intervertebral cage (1) within or outside the treated intervertebral space (E). This complete plate (33) also comprises an opening (330) enabling introduction of the graft into the cage (1) after the cage is placed in the intervertebral space.

In one embodiment represented in FIGS. 1b, 5a and 5b, a fixation device comprises a plate called complete plate (33) united with the small rod (23). Small rod (23) includes two locking studs (24, 25) perpendicular to the longitudinal axis of rod (23). Studs (24, 25) are housed in the two bores (121, 122) of the intervertebral cage (1). This complete plate (33) extends outside the intervertebral space (E) to be treated and is coupled to the exterior surface of the two vertebrae surrounding the intervertebral space (E) to be treated. The use of locking studs (24, 25) rather than pins makes it possible to use a softer material that is forced into the face of the vertebra, but on the other hand has the advantage of being transparent during radiography. The part of the piece connecting the small rod (23) and the complete plate (33) has a "T" shape in its section along a plane containing the axis of the spine.

This complete plate (33) includes at least two bores (331, 332) each of which receives a bone anchoring screw (4) of a known type. Screw (4) is fixed in the body of the corresponding vertebra and inserted into the face of the vertebra to prevent migration of the intervertebral cage (1) within or outside the treated intervertebral space (E).

In the embodiment illustrated in FIGS. 3a and 5a, each of the two opposite ends of the small rod (23) connecting the locking studs and the complete plate (33) has a rounded protuberance contacting the walls of the intervertebral cage (1). The rounded protuberances are clipped by elastic deformation in a housing (13) arranged in the wall opposite the intervertebral cage (1). The clipping of the protuberances (233) in the housings (13) makes it possible to maintain the cage (1) and the plate (33) together during positioning of the unit or after positioning.

In one embodiment, to prevent the anchoring screws from loosening, for example under the effect of the movements of the spine, the bores in plate (33) that receive the screws in a plane parallel to the plate (33) have a section slightly lower than the interior of the plate at the level of their opening on the surface opposite the vertebra; the surface opposite the vertebrae is called an external surface area. The heads of the screws have a part of a section greater than that of the external opening of the bore. Thus, once the screw has been screwed to where the large part of the head of the screw has penetrated the interior of the bore under force, the elasticity of the material forming the plate retains the screw head within the bore, limiting the risks of later loosening. This complete plate (33) also comprises an opening (330) enabling introduction of the graft into the cage (1) after positioning of the cage in the intervertebral space.

In one embodiment the plate (31, 32, 33) of the fixation device includes at least one bore (311, 321, 331, 332) for receiving a bone anchoring screw (4) which is located in a position shifted relative to a plane containing the axis of the spine. Thus, it is possible to treat two adjacent intervertebral spaces by using fixation plates and by positioning these plates in staggered rows. The shifted position of the bores in the plates enables the plates to be fixed in place by different screws located on the same vertebra and at the same height along the axis of the spine.

In one embodiment, all or part of the device according to the invention is made from a radiotransparent material, for example from PEEK, which makes it possible to monitor the development of bony tissues within the cage by radiography. In spite of that, for verification that the elements of the device are not displaced, it is possible to fix one or more of the elements with a radio marker containing, for example, a small piece of non-radiotransparent material.

Therefore, according to the applications it is possible to position an intervertebral cage (1) in different ways, simply by using one type or another of fixation device. The same intervertebral cage (1) can, for example, be positioned:
   either alone,
   or provided with a fixation device with pins (21, 22, 23),
   or provided with a fixation device with pins and a top (32) or bottom (33) hemiplate,
   or provided with a fixation device with pins and with a complete plate (33),
   or provided with a top (32) or bottom (31) hemiplate added by locking studs (24, 25),
   or provided with a complete plate (33) added by locking studs (24, 25).

Such modularity makes it possible for the surgeon to choose the type of fixation during the surgery and according to the anatomic conditions he encounters, by having at his disposal a reduced number of components among which to choose.

The fixation device that includes pins or a plate or both, can be later removed (for example during a new surgery) without significant destruction of the arthrodesis. In fact, this device may no longer be necessary after reinforcement of the arthrodesis, although providing discomfort, either for the patient or for similar treatment of an adjacent intervertebral space.

It must be obvious for persons skilled in the art that the present invention makes possible embodiments under numerous other specific forms without leaving the field of application of the invention as claimed. As a result, the present embodiments must be considered as illustration, but may be modified in the field defined by the scope of the fixed claims, and the invention must not be limited by the details given above.

What is claimed is:

1. A rigid, elongated anchor for an intervertebral device comprising:
   an insertion end having a projection part configured for insertion into a vertebra;
   a retention end having at least one protuberance configured to retain the anchor to the device; and
   a tongue-like body between the insertion end and the retention end.

2. The anchor of claim 1 in which the projecting part comprises a V-shaped tongue.

3. The anchor of claim 2 in which reliefs forming teeth are disposed along the tongue-like body.

4. The anchor of claim 3 in which the at least one protuberance is configured to clip to an intervertebral device.

5. The anchor of claim 1 comprising plural projecting parts.

6. The anchor of claim 5 in which the plural projecting parts comprise V-shaped tongues.

7. The anchor of claim 6 in which reliefs forming teeth are disposed along the tongue-like body.

8. The anchor of claim 1 in which the projecting part is sharpened.

9. An intervertebral implant device, the device comprising:
   an elongated receptacle configured to receive from an edge of the device an elongated, rigid anchor having a tongue-like body and to project a vertebral insertion end of the anchor from an upper or lower side of the device; and
   a housing configured to receive a protuberance on the anchor and hold the device against the anchor.

10. The intervertebral device of claim 9 in which the elongated receptacle is further configured to project the vertebral insertion end of the anchor from an upper or lower side of the device at an acute angle to said upper or lower side of the device.

11. The intervertebral device of claim 10 in which a wall of the elongated receptacle is formed at least in part by a thinned-down portion of an edge of the device.

12. The intervertebral device of claim 11 further comprising teeth on a surface along one or both of the upper and lower sides of the device.

13. The intervertebral device of claim 12 in which at least a portion of the device is made of a radiotransparent material.

14. The intervertebral device of claim 13 further comprising a radio marker.

15. The intervertebral device of claim 9 comprising plural elongated receptacles.

16. The intervertebral device of claim 9 having edges of nonuniform height.

17. The intervertebral device of claim 9 in which the receptacle comprises a stop for abutment of a retention end of the anchor.

18. A combination comprising the anchor and the implant of claim 9, in which the implant further comprises a stop for abutment of the retention end of the anchor.

19. The combination of claim 18 in which the anchor comprises plural projecting parts forming a V-shaped tongue.

20. The combination of claim 18 in which reliefs forming teeth are disposed along the tongue-like body.

* * * * *